(12) United States Patent
Pona

(10) Patent No.: US 11,478,232 B2
(45) Date of Patent: Oct. 25, 2022

(54) PUNCH BIOPSY DEVICE

(71) Applicant: Adrian Pona, Tecumseh (CA)

(72) Inventor: Adrian Pona, Tecumseh (CA)

( * ) Notice: Subject to any disclaimer, the term of this patent is extended or adjusted under 35 U.S.C. 154(b) by 552 days.

(21) Appl. No.: 16/536,433

(22) Filed: Aug. 9, 2019

(65) Prior Publication Data
US 2020/0046326 A1 Feb. 13, 2020

Related U.S. Application Data

(60) Provisional application No. 62/716,622, filed on Aug. 9, 2018.

(51) Int. Cl.
*A61B 10/02* (2006.01)
*A61B 10/06* (2006.01)
*A61B 17/3205* (2006.01)

(52) U.S. Cl.
CPC ...... *A61B 10/0275* (2013.01); *A61B 10/0266* (2013.01); *A61B 10/06* (2013.01); *A61B 17/32053* (2013.01); *A61B 2010/0208* (2013.01)

(58) Field of Classification Search
CPC .............. A61B 10/06; A61B 17/32053; A61B 10/0275; A61B 10/0266; A61B 2010/0208; A61B 2017/00761
See application file for complete search history.

(56) References Cited

U.S. PATENT DOCUMENTS

| 4,881,550 A * | 11/1989 | Kothe ............. A61B 10/02 600/565 |
| 5,357,974 A | 10/1994 | Baldridge |
| 5,515,861 A | 5/1996 | Smith |
| 5,776,075 A | 7/1998 | Palmer |
| 5,820,630 A * | 10/1998 | Lind ............. A61B 10/06 606/208 |
| 6,139,508 A * | 10/2000 | Simpson ............. A61B 10/06 600/564 |
| 6,155,989 A | 12/2000 | Collins |
| 2004/0167429 A1 | 8/2004 | Roshdieh et al. |
| 2004/0167430 A1 | 8/2004 | Roshdieh et al. |
| 2005/0113854 A1 | 5/2005 | Uckele |
| 2005/0131313 A1 | 6/2005 | Mikulka et al. |
| 2005/0256425 A1 | 11/2005 | Pursiner |
| 2006/0224084 A1 | 10/2006 | Vetter et al. |

(Continued)

FOREIGN PATENT DOCUMENTS

| EP | 0720442 A | 7/1996 |
| WO | 2013166443 A1 | 11/2013 |

OTHER PUBLICATIONS

Christopher J. Huerter, "Simple Biopsy Techniques," In: Wheeland RG (ed ), Cutaneous Surgery, Philadelphia, PA: W. B. Saunders, 1994; pp. 159-170.

(Continued)

*Primary Examiner* — David J. McCrosky
(74) *Attorney, Agent, or Firm* — Warn Partners, P.C.

(57) ABSTRACT

A hand held instrument for harvesting a biopsy sample is provided. The instrument includes a housing, an annular blade on a distal end of said housing for cutting axially cutting a biopsy, a transverse blade unit for transversely cutting the biopsy, and a plunger unit positioned within the housing ejecting the biopsy sample away from inside the housing after said biopsy sample has been transversely cut.

18 Claims, 9 Drawing Sheets

(56) References Cited

U.S. PATENT DOCUMENTS

2007/0249960 A1 10/2007 Williamson, IV
2008/0058673 A1 3/2008 Jansen et al.
2009/0018467 A1 1/2009 Chiu et al.
2016/0270770 A1 9/2016 McGhie et al.

OTHER PUBLICATIONS

A. H. Rotstein and H. Rotstein, "The use of Terson lens capsule forceps when performing punch biopsy of the skin," Australia Journal of Dermatology, 1997; vol. 38, pp. 222-223.
Neil A. Swanson, MD, Ken K. Lee, MD, Annalisa Gorman, MD, Han N. Lee, MD, "Biopsy techniques. Diagnosis of melanoma," Elsevier Science (USA), Dermatol. Clin 20, 2002; pp. 677-680.
Thomas J. Zuber, M.D., "Punch Biopsy of the Skin," Am. Fam. Physician, Mar. 15, 2002; vol. 65, pp. 1155-1158.
Mohamed Abdel-Monaem Abdel-Aal, MD, and Hussein M. M. Hassab-El-Naby, MD, "Surgical Pearl: The use of a wooden toothpick for the removal of a specimen from the biopsy site," Journal of the American Academy of Dermatology, 2003; vol. 48, p. 115.
T. Burns, S. Breathnach, N. Cox, C. Griffiths (eds), "Dermatological surgery," Rook's Textbook of Dermatology, vol. 4, 7th edn. Oxford: Blackwell Science, 2004; vol. 78, pp. 1-37.
"Therapeutic Guidelines: Dermatology," Version 2. North Melbourne: Therapeutic Guidelines Limited, 2004; pp. 8-13.
Richard A. Krathen, MD, and Ida F. Orengo, MD, "In a Pinch," American Society for Dermatologic Surgery, Inc., 2004 vol. 30, p. 1599.
European Search Report for European Patent Application No. 19189204 dated Feb. 19, 2020.

\* cited by examiner

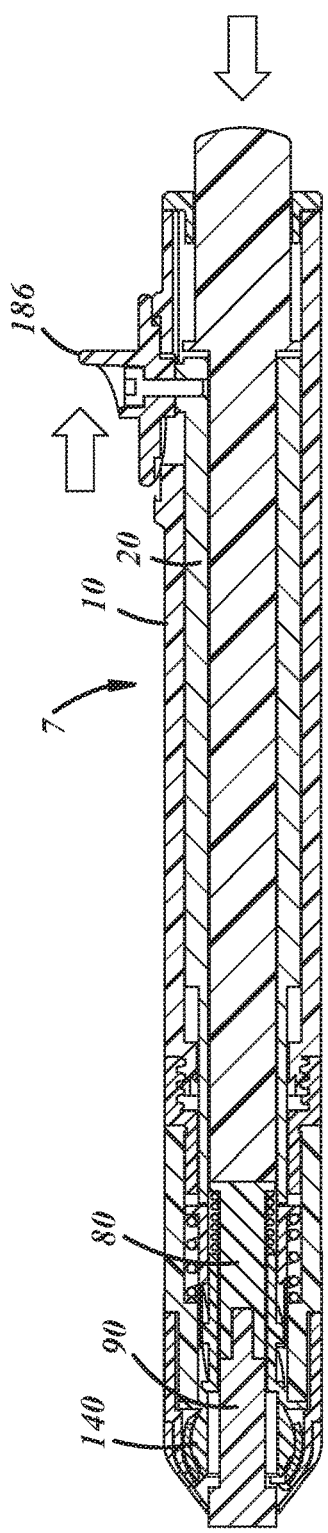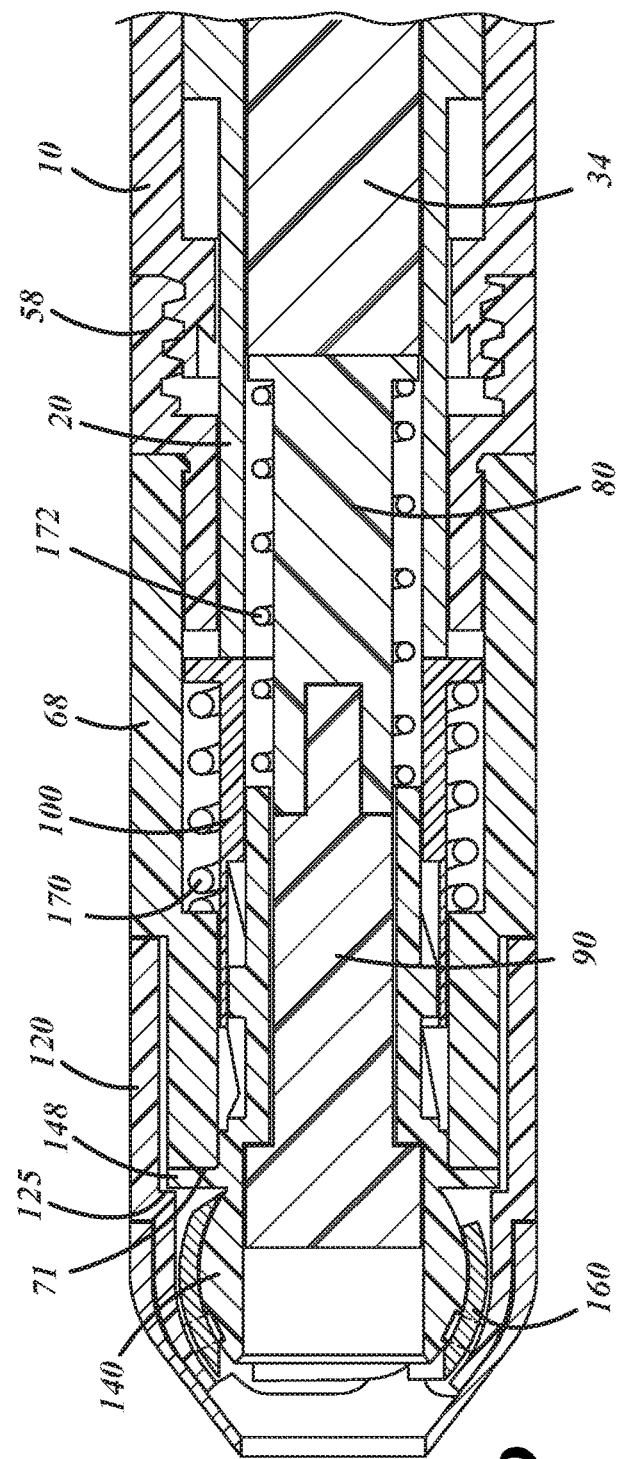
FIG. 4C
FIG. 4D

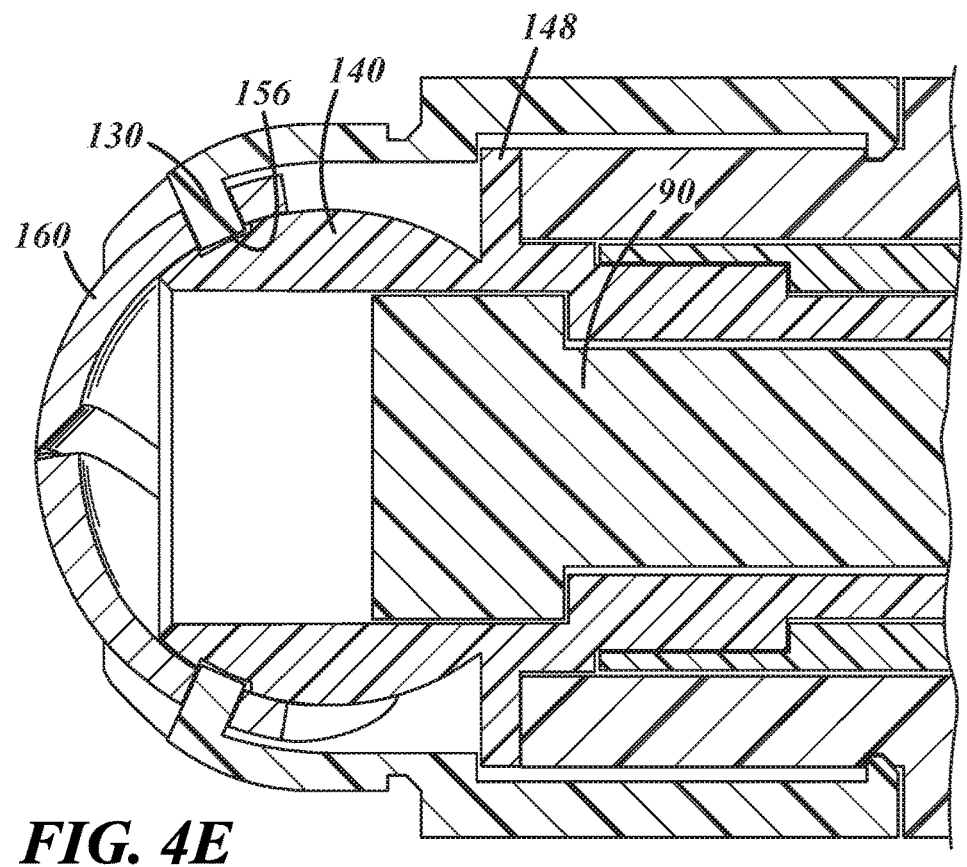
*FIG. 4E*
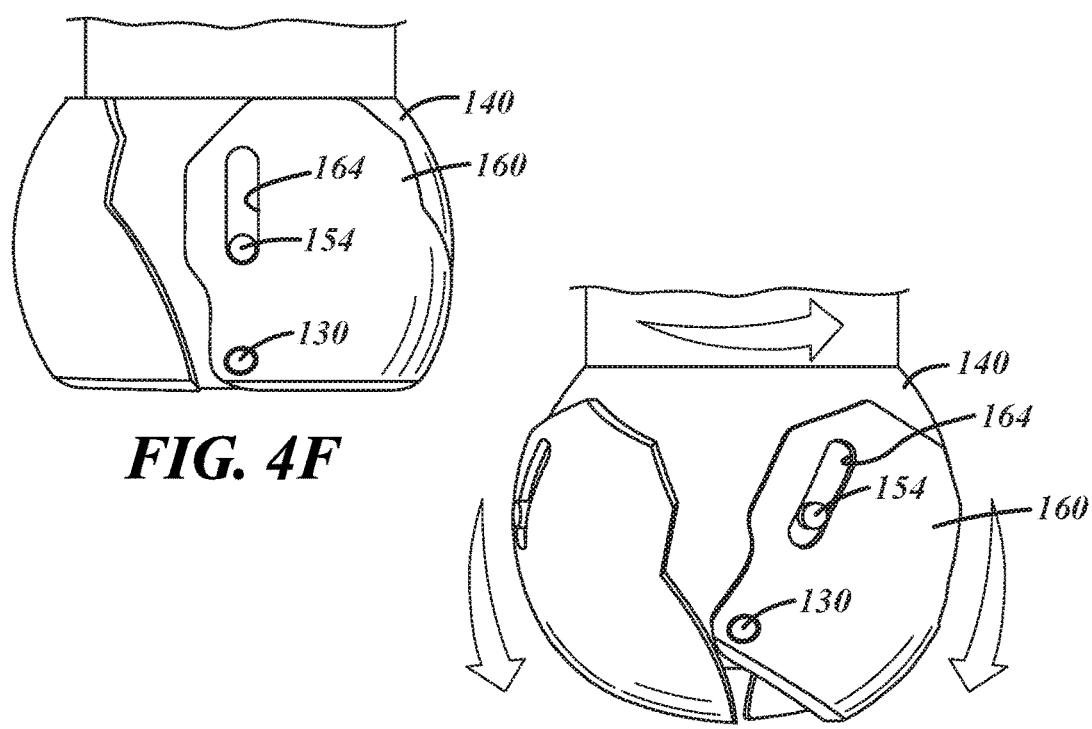
*FIG. 4F*
*FIG. 4G*

PUNCH BIOPSY DEVICE

FIELD OF THE INVENTION

This unique invention pertains to medical techniques, biopsy tools instruments and devices for sampling epidermal, dermal, and subcutaneous tissue in the hopes to acquire knowledge of the patient's health status. This invention is a punch biopsy with base excision and tissue sample ejection properties.

BACKGROUND OF THE INVENTION

The skin, from superficial to deep, is categorized into the epidermis, dermis and subcutaneous tissue. Many important structures, such as arteries, veins, nerves and white blood cells travel and reside in the skin. The skin is the largest organ in the body. Due to its priority to cover a vast area, many internal pathologies precipitate cutaneous manifestations. Furthermore, the skin acts as a barrier against dangerous chemicals and microorganisms and helps retain hydration of the body.

Skin biopsies are conducted to provide valuable information for patients. They may be used for diagnosis, treatment, or aesthetic reasons. There are two common types of biopsies used in practice; shave and punch biopsy. For the purpose of this invention, special focus will be made with punch biopsies.

Punch biopsies are performed using a skin punch instrument with a distal annular blade, forceps, and scissors. Before removal of the tissue, local anesthesia is infiltrated in the predetermined location. The punch instrument is placed over the intended spot to biopsy, then rotated clockwise and counter clockwise to form a circular incision. Once met with the proper depth, most commonly the subcutaneous tissue, the punch instrument is placed aside, forceps are used to elevate the incised annular specimen and the base is cut with scissors. The specimen is then placed in a specimen bottle for histopathological examination. Punch biopsies can be performed in numerous different sizes ranging from 2 mm to 15 mm. Once hemostasis is achieved, a simple suture is placed for healing purposes.

Limitations for punch biopsies include tissue crush artefact. When detaching the cylindrical tissue using forceps or a needle to lift the sample, the tissue manipulation may cause crushing artefacts when looking at the biopsied tissue under the microscope. This intervention may negatively influence the primary objective of diagnosing the condition. The risk of a needle-stick injury is also increased from the use of a needle to lift the tissue.

Another limitation is the risk of tissues being lodged in the cylindrical distal end. Solutions that physicians exercise to retrieve the sample include needle extractions and other means of expulsion. Tissue lodging is also seen commonly when small millimeter punch biopsies are used with one hand to rotate and scoop the sample. By using a rotating and angled force, parallel to the patient's skin, to sever the bottom of the tissue sample, lodging is a common complication.

Some physicians use a one-handed technique to punch out a tissue sample. As mentioned previously, the punch device is twisted into the necessary depth. Once reached, the instrument is angled parallel to the subject's skin while simultaneously twisting to sever the subcutaneous cord that connects the base. This technique benefits by only using one hand, an extra hand to stop the bleeding and no need to use forceps and scissors. Limitations include crush artefact, lodging of sample, and failure to sever the base of the sample. It is desirable to provide a punch biopsy instrument that overcomes the various problems as described above in a manner that is superior to instruments known in the prior art.

SUMMARY OF THE INVENTION

To make manifest the above delineated and other manifold desires, a revelation of the present invention is brought forth. In a preferred embodiment, the present invention brings forth a freedom of a hand held instrument for harvesting a biopsy sample. The instrument includes a housing, an annular blade on a distal end of said housing for cutting axially cutting a biopsy, a transverse blade unit for transversely cutting said biopsy, and a plunger unit positioned within said housing ejecting said biopsy out of said housing after said biopsy has been transversely cut.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4C is an sectional view similar to that of FIG. 4A illustrating operation the punch ejection unit of the biopsy instrument;

FIG. 4D is an enlargement of the biopsy harvesting instrument shown in FIG. 4A;

FIG. 4E is an enlargement of a portion of the biopsy harvesting instrument shown in FIG. 4D with a portion of an angular blade being removed for clarity of illustration;

FIG. 4F is a schematic view of the transverse blade unit in the non-actuated position;

FIG. 4G is a schematic view similar to that of 4F after illustrating operation of the transverse blade unit after initial actuation;

DETAILED DESCRIPTION OF THE PREFERRED EMBODIMENTS

The following description of the preferred embodiment(s) is merely exemplary in nature and is in no way intended to limit the invention, its application, or uses.

Figure 5:
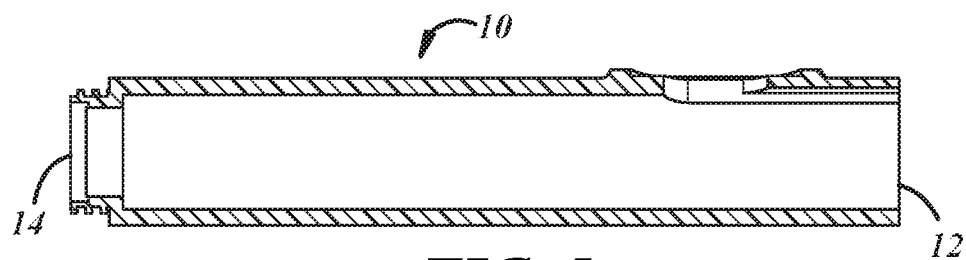
FIG. 5 is a side sectional view of a top housing the present invention shown in FIG. 1.
Figure 6:
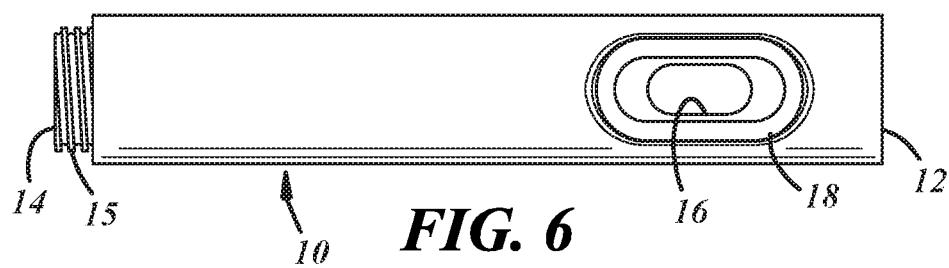
FIG. 6 is a side elevational view of the top housing shown in FIG. 5.

Referring to FIGS. 1 through 32, a hand held instrument 7 for harvesting a biopsy is provided. The instrument 7 is particularly helpful in harvesting skin biopsies. The instrument 7 has a tubular like multiple member housing 9. The tubular housing 9 includes a top housing 10 (FIGS. 5 and 6).

The top housing 10 has an open top 12 and an open bottom 14. The top housing bottom 14 has an exterior threaded section 15. Top housing 10 has an elongated hole 16. Encircling the hole 16 is a molding 18. The top housing 10 is typically fabricated from an ABS (Acrylonitrile Butadiene Styrene) plastic or other suitable material. Typical diameters of the upper housing range between 18 and 15 mm. Typical wall thicknesses can be between 2.3 to 1.95 mm.

Figure 7:
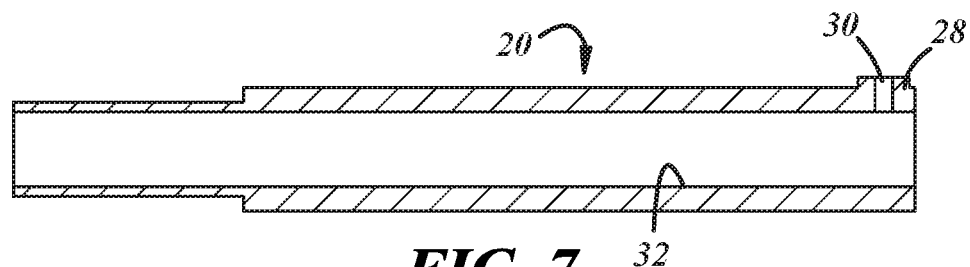
FIG. 7 is a sectional of a cutting tab pusher utilize in the biopsy harvesting instrument shown in FIG. 1.
Figure 8:
FIG. 8 is a side elevational view of the cutting tab pusher shown in FIG. 7.
Figure 32:
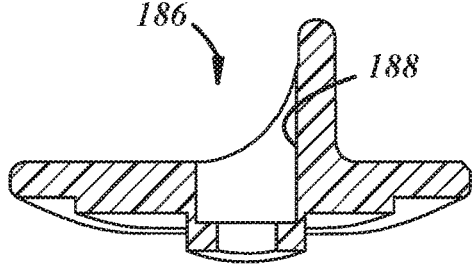
FIG. 32 is a view taken along line 32-32 of the push tab shown in FIG. 31.
Figure 32:
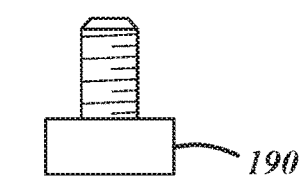

Slidably mounted within the top housing 10 is a cutting tab pusher 20 FIGS. 7-8). The cutting tab pusher 20 is a hollow tubular member having a thick walled section 22 and a thin walled section 24 separated by an exterior shoulder 26. The cutting tab pusher 20 has a constant dimensional inner diameter 32. The cutting tab pusher 20 also has a transverse's stud or flange 28 having an interior 30 that is threaded for receiving a headed fastener 190 (FIG. 32). The cutting tab pusher 20 is fabricated from 6061 alloy aluminum or other suitable substitute thereof.

Figure 9:
FIG. 9 a side elevational view of an eject pusher utilize in the biopsy harvesting instrument shown in FIG. 1.

Slidably mounted in the cutting tab pusher 20 is an eject pusher 34 (FIG. 9). The eject pusher 34 has a cylindrical stem 36. At the top of the stem 36 is a cylindrical shoulder 38. The shoulder 38 is topped by a slightly smaller diameter head 40. The eject pusher 34 is typically fabricated from an ABS plastic or other suitable material.

Figure 10:
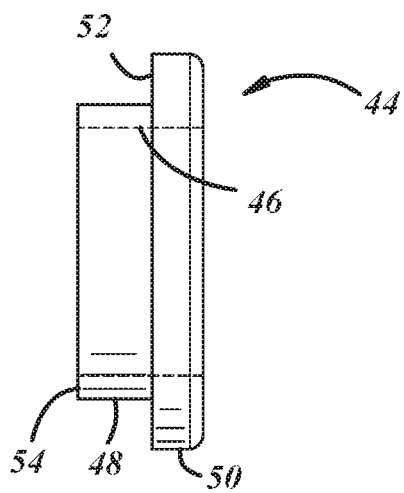

Encircling the head 40 of the eject pusher and topping off the top housing 10 is a top housing cap 44 (FIG. 10). The top housing cap 44 has an inner diameter 46 which encircles the eject pusher head 40. A smaller outer diameter section 48 is joined to a larger outer diameter section 50. The smaller diameter section 48 is inserted in the top 12 of the top housing 10 and an under portion 52 of the larger diameter sets on top of the top housing 10 and the smaller outer diameter section 48 by adhesive or interference fit connects the top housing cap 44 with the top housing 10. An under portion 54 of the top housing cap smaller outer diameter section acts as a vertical stop against the shoulder 38 of the eject pusher to limit the eject pusher's 34 vertical upward travel with respect to the top housing 10. The top housing cap 44 is typically fabricated from an ABS plastic or other suitable material.

Figure 11A:
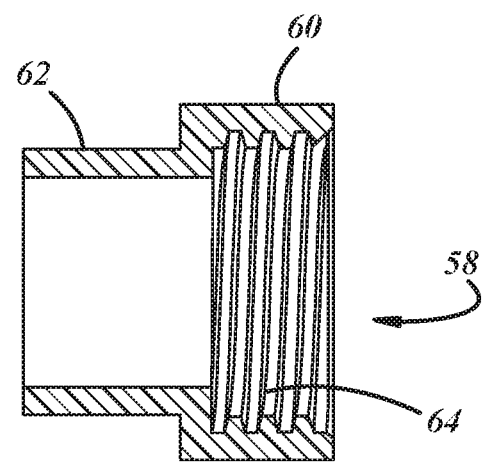
FIG. 11A is a section view taken along lines 11A-11A of FIG. 11B of a cartridge housing thread of the present invention.
Figure 11B:
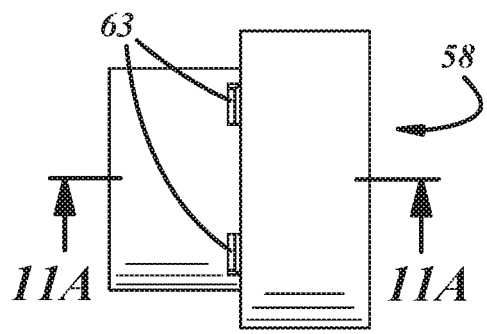
FIG. 11B is a side elevational view the cartridge housing thread.

Positioned at the bottom 14 the top housing 10 and threadably connected there to is a cartridge housing thread 58 (FIGS. 11A and 11B). The cartridge housing thread 58 has a large diameter section 60 joined to a smaller diameter section 62. The cartridge housing thread has an interior threaded section 64 which engages with threaded section 15 of the top housing 10. Connector slots 63 are provided for acceptance of connecter tabs as to be explained later. The cartridge housing thread 58 can be fabricated from ABS plastic or other suitable material.

Figure 12:
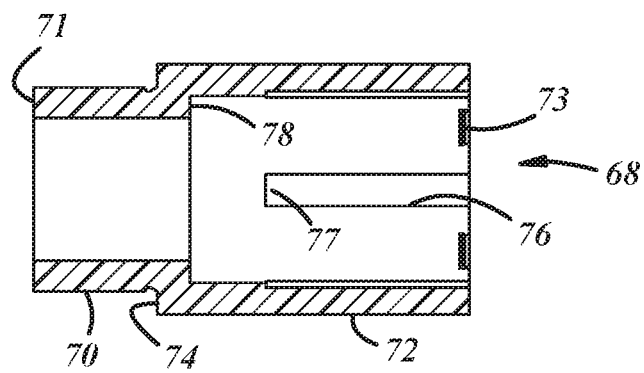
FIG. 12 is a view taken along line 12-12 of FIG. 14 of a cartridge main housing.
Figure 13:
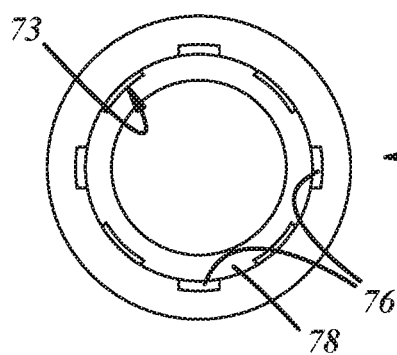
FIG. 13 is a top elevational view of the cartridge main housing shown in FIG. 12.
Figure 14:
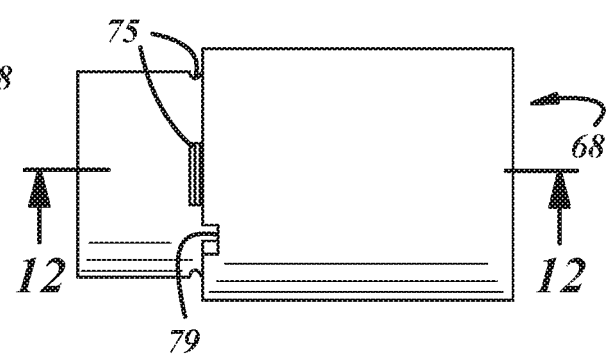
FIG. 14 is a side elevational view of the cartridge main housing shown in FIGS. 12 and 13.

Referring to FIGS. 12 through 14, connected with the cartridge housing thread 58 at a bottom end is a cartridge main housing 68. Cartridge main housing 68 has a small diameter section 70 and a large diameter section 72. Interior inwardly projecting connector tabs 73 are provided to snap fit connect the cartridge main housing 68 with the cartridge housing thread 58 by insertion into the connector slots 63. The cartridge main housing 68 is typically fabricated from ABS plastic or other suitable material. The cartridge main housing 68 has an internal shoulder 78 and external shoulder 74 between the large diameter section 72 and the small diameter section 70. An interior of the large diameter section 72 additionally has an axial longitudinal groove 76 having an axial bottom 77. An exterior of the cartridge main housing small diameter section has connector tab slots 75 and the exterior of large diameter section 72 has an alignment slot 79 on its exterior near the bottom.

Figure 15A:
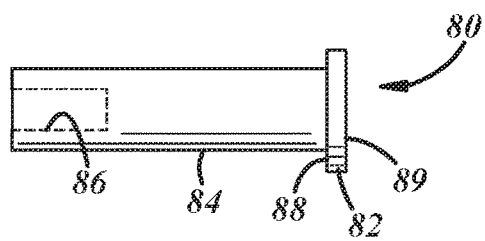
FIG. 15A is a side elevational view of a top plunger of the present invention.

Positioned underneath the eject pusher 34 and having a top surface 89 spring biased in contact there with, is a cartridge upper plunger 80 (FIG. 15A). Cartridge upper plunger 80 has a head 82 and a stem 84. The stem 84 has a cylindrical shape blind inner bore 86 its lower end. A shoulder 88 of the cartridge upper plunger provides a spring mount for a biasing spring 172. Typically the cartridge upper plunger 80 is fabricated from an ABS plastic or other suitable material.

Figure 15B:
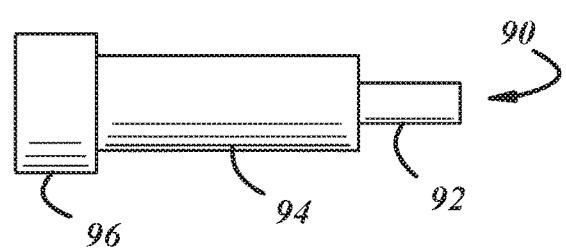
FIG. 15B is a side elevational view of a bottom plunger of the present invention.

Positioned directly underneath cartridge upper plunger 80 is a cartridge lower plunger 90 (FIG. 15B). The cartridge lower plunger 90 has a stem 92, a mid-body 94, and a head 96. Optionally the bottom of the head 96 can be coated with an adhesive to make a biopsy sample stick thereto. The cartridge lower plunger stem 90 through an interference fit with the annular bore 86 of the cartridge upper plunger, joins the upper and lower plungers together. Additionally the cartridge lower plunger 90 and cartridge upper plunger 80 can be joined together via friction fit, or glue, or thread, or interference snap fit. The cartridge lower plunger 90 can be fabricated from the same material that the cartridge upper plunger 80 can be fabricated from.

Figure 15C:
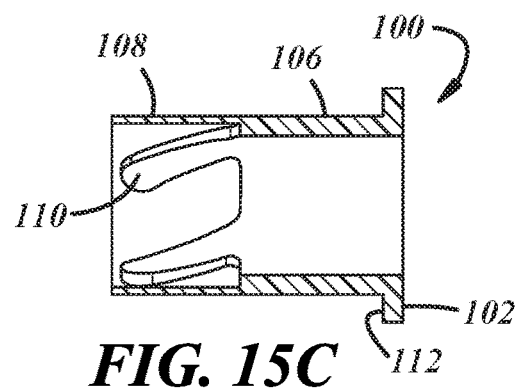
FIG. 15C is a view taken along line 15C-15C of FIG. 16 of a blade pusher.
Figure 16:
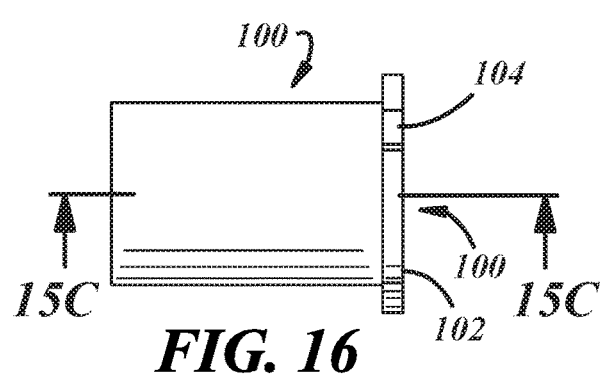
FIG. 16 is a side elevational view of blade pusher shown in FIG. 15C.
Figure 17:
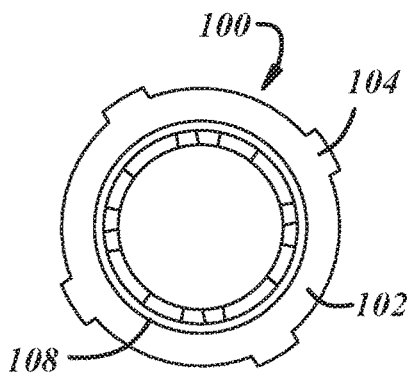
FIG. 17 is a top elevational view of blade pusher shown in FIG. 15C and FIG. 16.
Figure 18:
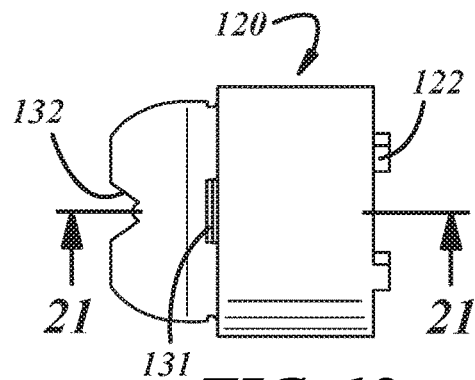
FIG. 18 is a side elevational view of a capture head in the biopsy harvesting instrument of the present invention.
Figure 19:
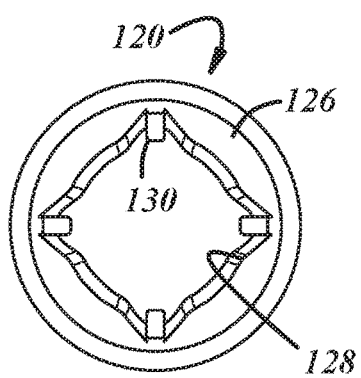
FIG. 19 is a bottom elevational view of the capture head shown in FIG. 18.
Figure 20:
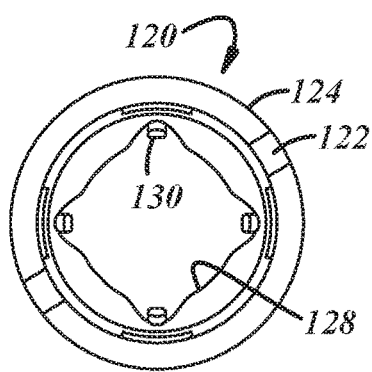
FIG. 20 is a top elevational view of the capture head shown in FIG. 18.
Figure 21:
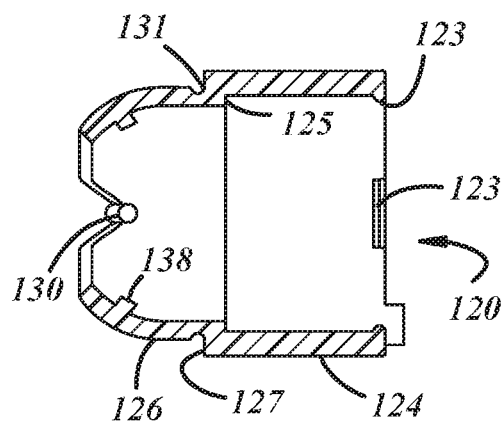
FIG. 21 is a section view of the capture head shown in FIG. 18 taken along lines 21-21.

Referring to FIGS. 15-17, encircling the upper and cartridge plungers 80, 90 is a linear motion blade pusher 100. The blade pusher 100 has a top flange 102. The top flange 102 has four geometrically spaced radially outward projecting alignment studs 104. Joined to the top flange 102 is a main body 106. Projecting downwardly from main body 106 is a skirt 108. An interior of the skirt 108 has integrally formed cam tabs 110. An under side of the top flange 102 intersection with the blade pusher main body 106 provides a shoulder and spring mount 112 for a biasing spring 170 (see FIG. 3). Typically, the cartridge blade pusher 100 is fabricated from an ABS plastic or other suitable material.

Referring to FIGS. 18-21, a capture head 120 is provided. The capture head completes the housing 9. The capture head 120 has along its top end assembly alignment studs 122. Along its interior surface adjacent to the top the capture head has inwardly projecting connector tabs 123. The capture head has a top body 124 and a crown 126. Between the capture head top body 24 and crown 126, the capture head has an inner shoulder 125 and an outer shoulder 127. Capture head 120 has a window 128. The capture head has four inwardly directed pivot pins 130 geometrically spaced apart from one another. The capture head 120 has connector tab slots 131. The connector head 120 has four arch ways 132. Typically the capture head 120 is fabricated from an ABS plastic or other suitable alternative.

Figure 22:
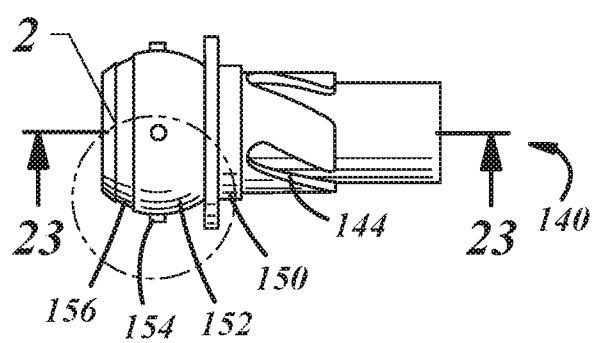
FIG. 22 is a side elevational view of the blade holder of the biopsy harvesting instrument shown in FIG. 1.
Figure 23:
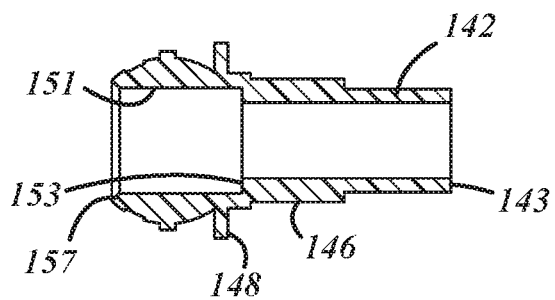
FIG. 23 is a section view along lines 23-23 of the blade holder shown in FIG. 22.
Figure 24:
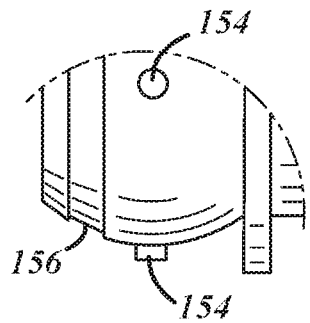
FIG. 24 is an enlarged view of a portion encircled of the blade holder shown in FIG. 22.
Figure 25:
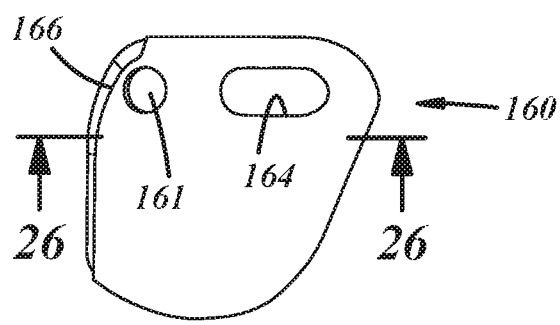
FIG. 25 is a plane elevational view of a transverse blade utilized in the biopsy harvesting instrument of the present invention.
Figure 26:
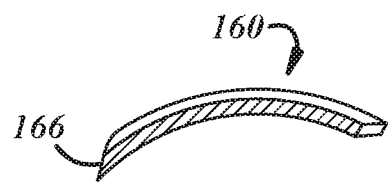
FIG. 26 is a section view taken along line 26-26 of FIG. 25.
Figure 27:
FIG. 27 is a bottom plan view of the transverse blade shown FIG. 25.
Figure 28:
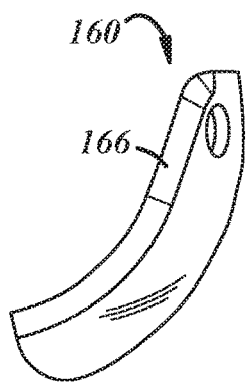
FIG. 28 is a top plan view the blade shown in FIG. 25.
Figure 29:
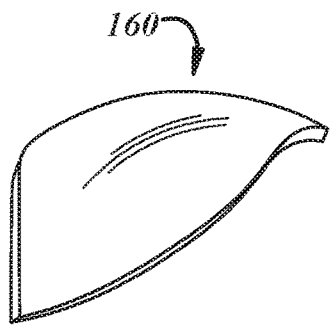
FIG. 29 is a side elevational view blade shown in FIG. 25.

Referring to FIGS. 22-24 there is provided a blade holder 140. The blade holder 140 has a skirt 142. A top surface 143 of the skirt 142 provides a stop for the spring 172. The blade holder 140 is stationary vertically. The blade holder has a flange 148 that is captured in between the inner shoulder 125 of the capture head and a bottom face 71 of the small diameter section 70 of cartridge main housing 68. The blade holder has cam slots 144 and cam slots integrally formed into a mid-body 146. Underneath mid-body 146 is a pedestal 150. The blade holder support flange 148 has connected thereto a pivot globe 152. Pivot globe 152 has four geometrically spaced pivot pins 154 projecting outwardly there from. Pivot globe 152 along its lower hemisphere has an annular groove 156. Groove 156 receives the four inwardly directed pivot pins 130 that project from capture head 120. The blade holder is typically fabricated ABS plastic other suitable material. The blade holder pivot globe 152 has an inner bore 151 to receive the head 96 of the lower cartridge plunger and an inner shoulder 153 to limit the upward position of the head 96. Inner bore 151 has an opening taper 157. Typically the blade pusher skirt 108 will have a diameter smaller than the diameter of the pivot globe.

Referring to FIGS. 25-29 on of four transverse cutting blades 160 for making a transverse cut is provided. Each transverse cutting blade has a hole 161 so that it may pivot about pivot pin 130 that project from the captive head. The pivot pin extreme end rides in the annular slot 156 of the pivot globe thereby preventing the blade 160 from dislodging for the pivot pin 130 (Shown in FIGS. 19 and 4E). The transverse cutting blade has an elongated blade slot 164. The transverse cutting blade has a sharpened cutting edge 166. The cutting blade 160 typically fabricated from, 316 stainless steel other suitable alternative. The transverse cutting blades 160 are curvilinear, having preferably a conic, more preferably a hemispherical shaped component in their shape.

Figure 4H:
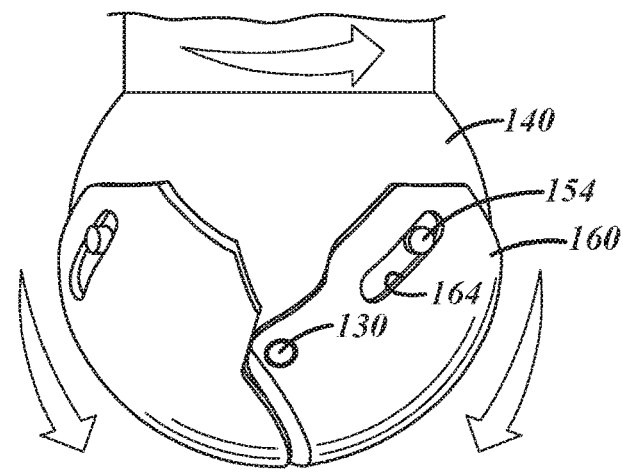
FIG. 4H is a schematic view similar to that of 4F after illustrating operation of the transverse blade unit upon completion of its cutting operation.
Figure 4I:
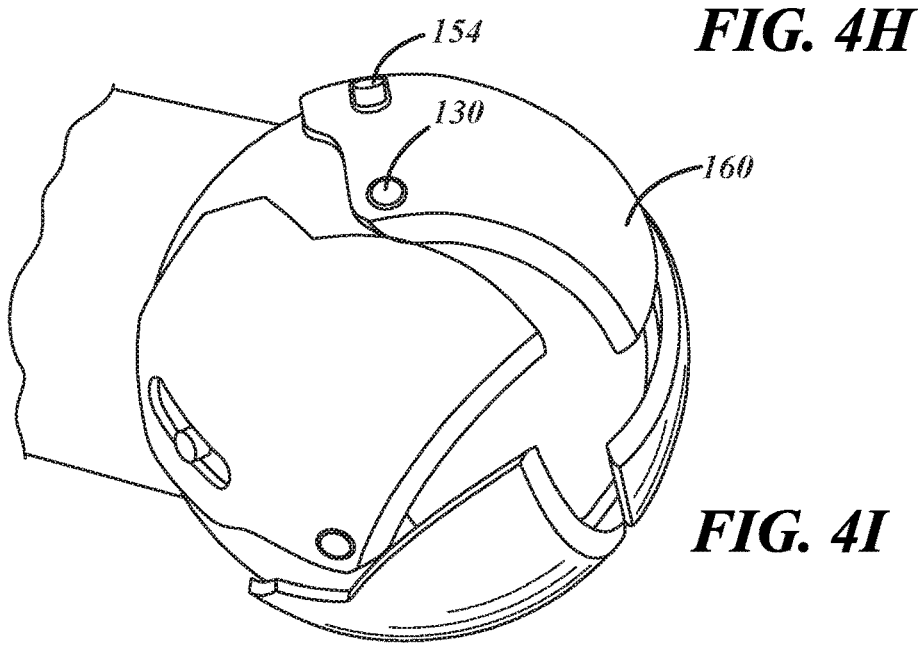
FIG. 4I is a schematic perspective view of the transverse blade unit shown previously in side elevation in FIG. 4G.
Figure 3:
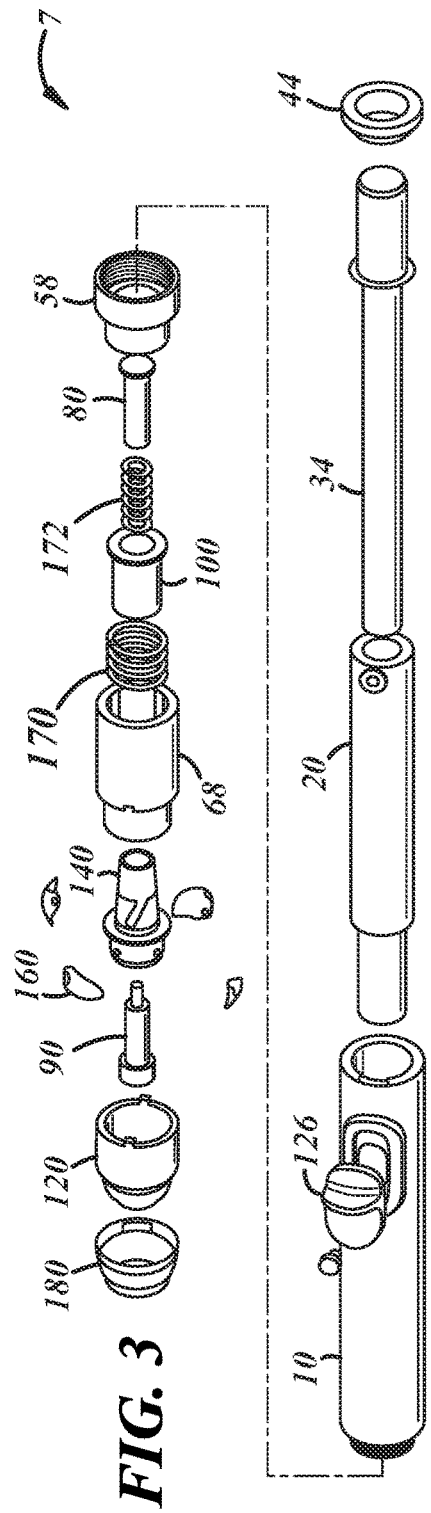
FIG. 3 is an exploded view of the biopsy harvesting instrument shown FIG. 1.
Figure 4A:
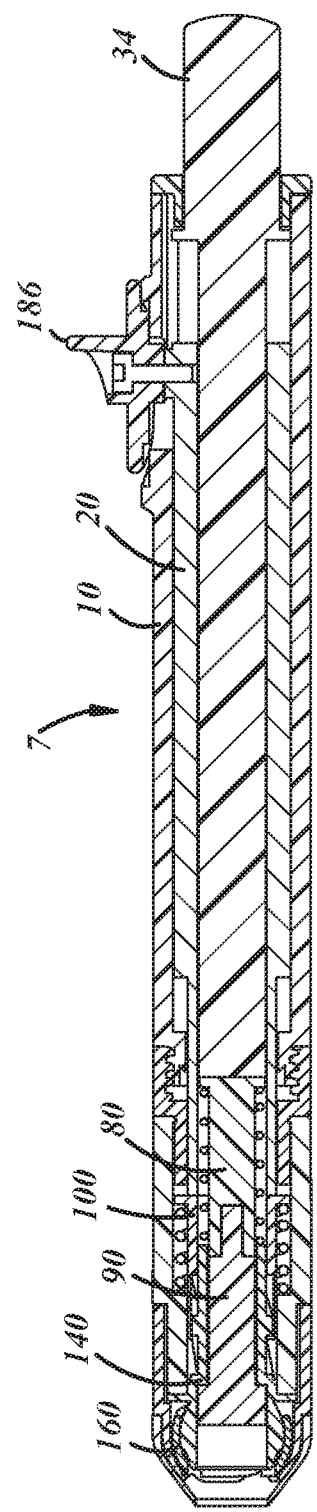
FIG. 4A is a sectional view of the biopsy harvesting instrument shown in FIG. 1.
Figure 4B:
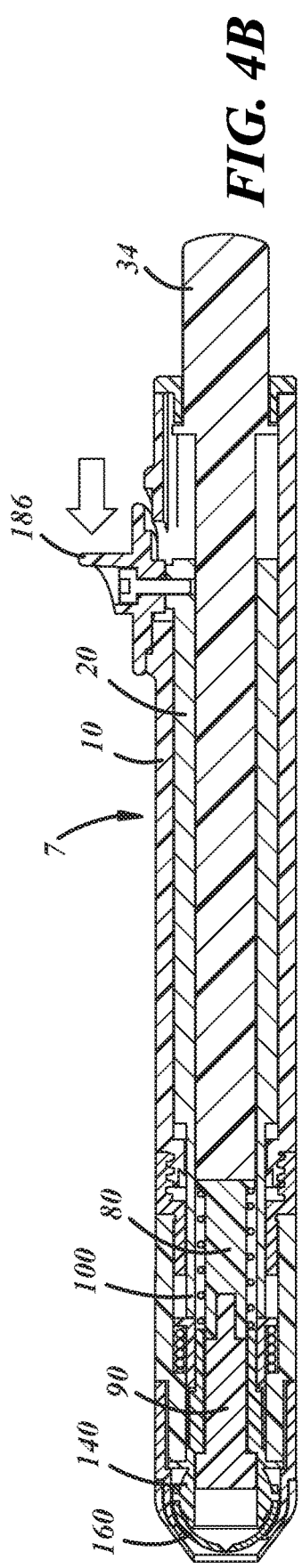
FIG. 4B is a sectional view similar to that of FIG. 4A illustrating the transverse blade unit of the biopsy harvesting instrument being activated.

As best shown in FIGS. 4A-4C, the coil spring 170 is pushed upward against contact shoulder 112 of blade pusher and bottoms out on an internal shoulder 78 of the cartridge main housing.

Figure 30:
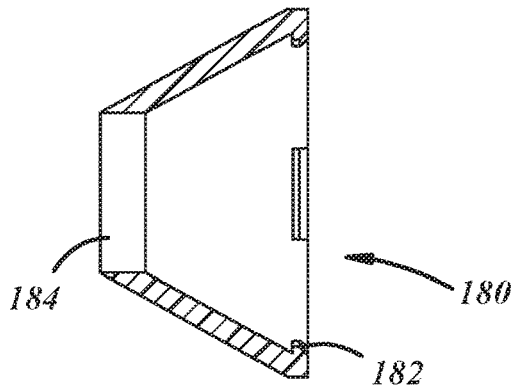
FIG. 30 is a section view of the annular blade on the distal end of the biopsy harvesting instrument shown in FIG. 1.

Referring to FIG. 30 on a distal end of the handle the annular cutting blade 180 is provided. Annular blade 180 has a connector tab 182 allowing it to the snap fitted into connector tab slots 131 of the capture head. The annular cutting blade 180 is typically fabricated from 316 stainless steel or other suitable alternatives. The annular blade 180 typically will have a one degree radially inward wedging taper in a direction toward the proximal (top) end of the instrument 7 on its inner diameter 184. The annular blade on its outer diameter typically will have an angle between 45-55 degrees and in many application will be angled between 50-52 degrees.

Figure 1:
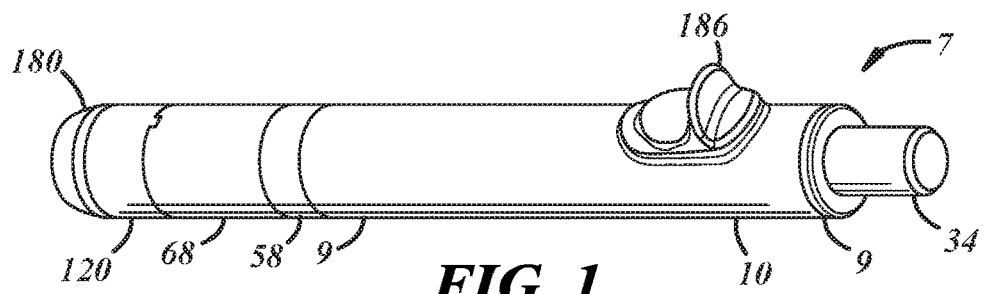
FIG. 1 is a perspective view of a preferred embodiment biopsy harvesting instrument of the present invention shown horizontally with it top end to the right.
Figure 2:
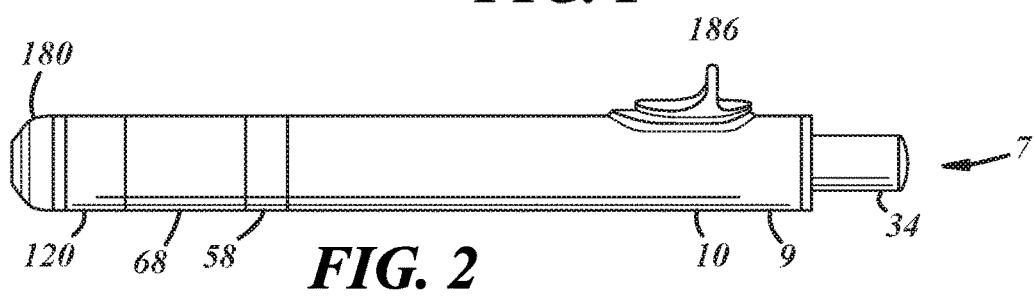
FIG. 2 is a side elevational view of the biopsy harvesting instrument shown in FIG. 1.
Figure 31:
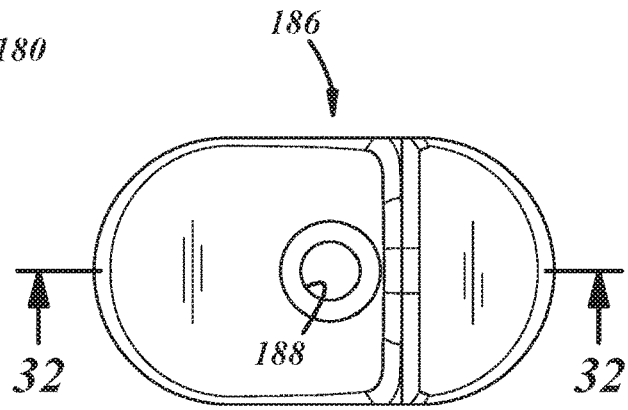
FIG. 31 is a side elevational view of a push tab utilized to activate the plunger unit of the biopsy harvesting instrument shown in FIG. 1.

Referring to FIGS. 1 and 31-32 a push tab 186 provided. The push tab 186 has a bore 188 to allow for insertion of a headed fastener 190 to connect the push tab with cutting tab pusher via opening 16 provided in the top housing 10.

In operation a physician or other medical professional takes the biopsy harvesting instrument 7 and pushes down while twisting the housing allowing the annular cutting blade 180 to make an axial annular cut in a patient's tissue, typically the skin. The physician then actuates the transverse blade unit pushing down on the push tab 186 causing the cutting tab pusher 20 to press down the blade pusher 100 (see Figure's 4B, 4E and 4F-G). The blade pusher 100 is prevented from, rotational motion by placement of its top flanged alignment studs 104 within the cartridge main housing axial grooves 76. The cam tabs 110 of the blade pusher interact with the cam slots 144 of the blade holder causing the blade holder to rotate causing movement of the pivot pins 154 in the elongated slots 164 of the blades 160 causing the blades 160 to rotate from an upper retracted position about pivot pins 130 of the capture head the blades 160 move to a lower cutting position making a scalping transverse cut of the skin sample that has already been cut in an axial position cut. Typically the blade holder 140 will rotate not more than 30° and typically in a range of 27-30°. To prevent the blades from wedging together, rotation of the blade holder 140 can be limited by the blade holder alignment studs 104 hitting the stop provided by the cartridge main housing groove 76 bottom 77. The skin sample is retained in the instrument 7 by the capture head 120. The plunger unit is utilized to push out the biopsy sample from the instrument 7 by pushing down on the head 40 of the eject pusher 34 causing the eject pusher 34 to press cartridge upper 80 and lower 90 plunger against the spring 172 allowing the head 96 of the cartridge lower plunger 90 to push out biopsy sample from its position between the blade holder 140 the capture head 120.

The various connector tab have a taper to facilitate upward movement for connection to an adjoining piece of the housing. The transverse blade unit and lower plunger are detachable for replacement by rotation of the cartridge housing thread 58. The remainder of the instrument 7 may be sterilized if required for reuse. Biopsy samples of different sizes can be harvested by simply clipping onto the capture head 120 an annular blade 180 with a different diameter.

In another embodiment (not shown) the blade holder is caused to rotate by a rotational portion of the housing preferably a lower portion of the housing.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A hand held instrument for harvesting a biopsy sample comprising:
    a housing;
    an annular blade on a distal end of said housing for axially cutting a biopsy;
    a retractable segmented hemispherical transverse blade unit for transversely cutting said biopsy; said retractable segmented hemispherical transverse blade unit including a blade holder radially within said transverse blades and a capture head encircling said transverse blades wherein said transverse blade unit have one of a blade holder and a capture head pin in slot type connection with said transverse blades and said blades additionally have a pivotal connection with said other one of said blade holder and a capture head; and,
    a plunger unit positioned within said housing for pushing said biopsy away from said housing after said biopsy has been transversely cut.

2. An instrument as described in claim 1 having a detachable transverse blade unit.

3. An instrument as described in claim 1 having four transverse blades.

4. An instrument as described in claim 1 wherein said pin in slot connection is made by a pin connected with said blade holder captured in an elongated slot in said transverse blade.

5. An instrument as described in claim 1 wherein said blade holder is rotated by a linear motion actuator.

6. An instrument as described in claim 5 wherein said actuator is a push tab extending on a side of said housing.

7. An instrument as described in claim 5 wherein said push tab engages a linear motion blade pusher having a cam relationship with said blade holder.

8. An instrument as described in claim 7 wherein said blade pusher has a positive stop to limit rotation of said blade holder.

9. An instrument as described in claim 1 wherein plunger unit is actuated by pushing down on a head on a top of said housing.

10. An instrument as described in claim 1 wherein said annular blade has a radially inward wedging taper in a proximal direction.

11. An instrument as described in claim 1 wherein said pivotal connection of said blade with one of said blade holder and said capture head is more adjacent to said annular blade than said pin in slot connection of said blade with said other of said blade holder and said capture head.

12. An instrument as described in claim 1 wherein said capture head has a pin projecting through a hole in said transverse blade and an end of said pin as captured in an annular slot of said blade holder.

13. An instrument as described in claim 1 wherein saki annular blade has a snap fit connection with said capture head.

14. An instrument as described in claim 13 wherein said pivotal connection of said blade with one of said blade holder and said capture head is more adjacent to said annular blade than said pin in slot connection of said blade with said other of said blade holder and said capture head.

15. A hand held instrument for harvesting biopsy comprising:
    a tubular like housing;
    an annular blade on a distal end of said housing for axially cutting a biopsy;
    a transverse blade unit for cutting transversely said biopsy, said transverse blade unit including a blade holder with a pin in slot connection with at least four transverse blades and said transverse blades having a pivotal connection with a capture head encircling said transverse blades and said transvers blade unit being actuated by a linear motion push tab extending from said housing; and
    a plunger unit positioned within said housing biasing said biopsy away from said housing after said biopsy has been transversely cut, said plunger unit being actuated by pushing down on a head of said housing.

16. An instrument as described in claim 15 wherein said blade holder has a pivot globe, and a skirt with a cam surface connected with said globe, and wherein said transverse blade unit includes a linear actuated blade pusher, said blade pusher having a skirt with a cam surface engaged with said cam surface of said blade holder and wherein said skirt of said blade pusher has a smaller diameter than the diameter of said pivot globe.

17. A method of harvesting a biopsy utilizing the instrument of claim 15 comprising:
    twisting the housing to make an annular axial cut into a patient's tissue while pushing said housing toward the patient's tissue;
    pushing down on said push tab to transversely cut said tissue with said transverse blade unit; and
    pushing down on a head of said housing to expel said biopsy tissue sample from said instrument.

18. A hand held instrument for harvesting biopsy comprising:
    a tubular like housing;
    an annular blade on a distal end of said housing for axially cutting a biopsy;
    a transverse blade unit for cutting transversely said biopsy, said transverse blade unit including a blade holder with a pin in slot connection with at least four hemispherical transverse blades and said transverse blades having a pivotal connection with a capture head encircling said transverse blades, said pivotal connection with said capture head including a pin projecting from said capture head projecting through a hole in said blades, said pin being captured in an annular groove in said blade holder and said transverse blade unit being actuated by a linear motion push tab extending for said housing; and
    a plunger unit positioned within said housing pushing said biopsy from said housing, said plunger unit being actuated by pushing down on a head of said housing, and said plunger unit having a plunger formed by an upper and lower plungers connected together.

\* \* \* \* \*